United States Patent [19]

Sauerwald et al.

[11] Patent Number: 4,670,567
[45] Date of Patent: Jun. 2, 1987

[54] PROCESS FOR THE PREPARATION OF 5,6-DIHYDRO-2H-THIOPYRAN-3-CARBOXALDEHYDE DERIVATIVES WHEREIN THE REACTIONS ARE CONDUCTED IN A HIGH BOILING MINERAL OIL WITHOUT A CATALYST

[75] Inventors: Manfred Sauerwald, Roedersheim-Gronau; Toni Dockner, Meckenheim; Wolfgang Rohr, Wachenheim; Gernot Reissenweber, Boehl-Iggelheim, all of Fed. Rep. of Germany

[73] Assignee: BASF Aktiengesellschaft, Ludwigshafen, Fed. Rep. of Germany

[21] Appl. No.: 758,812

[22] Filed: Jul. 25, 1985

[30] Foreign Application Priority Data

Jul. 25, 1984 [DE] Fed. Rep. of Germany ....... 3427404

[51] Int. Cl.$^4$ ............................................ C07D 335/02
[52] U.S. Cl. ..................................................... 549/13
[58] Field of Search ......................................... 549/13

[56] References Cited

U.S. PATENT DOCUMENTS 3,733,336  5/1973  Wagner et al. ........................ 514/13
4,289,777  9/1981  Albrecht et al. ...................... 514/312
4,438,282  3/1984  Lardon et al. ......................... 549/13

FOREIGN PATENT DOCUMENTS 1919504  4/1969  Fed. Rep. of Germany ........ 549/13

OTHER PUBLICATIONS

J. Chem. Soc., 1941, 404–408.
J. Org. Chem., 42, 2123–2126 (1977).
J. Chem. Soc., 1951, 2123–2125.
Z. Lebensm. Unters. Forsch, 170-34-35 (1980).

Primary Examiner—Henry R. Jiles
Assistant Examiner—J. G. Mullins
Attorney, Agent, or Firm—Keil & Weinkauf

[57] ABSTRACT

5,6-Dihydro-2H-thiopyran-3-carboxaldehydes of the formula

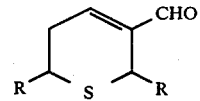

where R denotes hydrogen or methyl, are prepared by a method in which acrolein or crotonaldehyde is reacted with hydrogen sulfide in a mineral oil whose boiling point is higher than those of the starting materials and of the end product, and the 5,6-dihydro-2H-thiopyran-3-carboxaldehyde is obtained by distillation. These aldehydes are important intermediates for the preparation of some crop protection agents.

7 Claims, No Drawings

PROCESS FOR THE PREPARATION OF 5,6-DIHYDRO-2H-THIOPYRAN-3-CARBOXALDEHYDE DERIVATIVES WHEREIN THE REACTIONS ARE CONDUCTED IN A HIGH BOILING MINERAL OIL WITHOUT A CATALYST

The present invention relates to a process for the preparation of 5,6-dihydro-2H-thiopyran-3-carboxaldehydes which are unsubstituted or methyl-substituted in the 2,5-position, by reacting acrolein or crotonaldehyde with hydrogen sulfide in a mineral oil. 5,6-Dihydro-2H-thiopyran-3-carboxaldehydes are important intermediates for the preparation of some crop protection agents.

The oldest of the conventional processes for the preparation of 5,6-dihydro-2H-thiopyran-3-carboxaldehyde is based on the reaction of 3-chloropropionaldehyde diethyl acetal with potassium sulfide and gives yields of less than 60% (J. Chem. Soc. 1941, 404–408). 3-Chloropropionaldehyde diethyl acetal is prepared from acrolein, ethanol and hydrogen chloride, in a yield of 80%.

The reaction of 3-thioacetoxypropanal with acrolein in methylene chloride and aqueous sodium hydroxide solution under phase-transfer conditions gives yields of about 85%. According to J. Org. Chem. 42 (1977), 2123–2126, the direct reaction of thioacetic acid with two equivalents of acrolein under phase-transfer conditions gives 5,6-dihydro-2H-thiopyran-3-carboxaldehyde in a yield of only 40%. 3-Thioacetoxypropanal is obtainable from acrolein and thioacetic acid in the presence of benzoyl peroxide, in a yield of 65% (J. Chem. Soc. 1951, 2123–2125).

In a process described in German Laid-Open Application DOS No. 1,919,504, yields of about 90% are obtained if acrolein is reacted with hydrogen sulfide in the presence of an acid or base in an autoclave under from 0 to 10 bar, and the reaction product is treated with an acid. The disadvantages of this process are that, in particular, chlorohydrocarbons, eg. chloroform, are used as solvents in the first reaction stage, and large amounts (from 10 to 50 mol%, based on acrolein) of mineral acids, eg. phosphoric acid or sulfuric acid, are required for the dehydration stage. Particularly where the highly corrosive compound phosphoric acid is used, this leads to problems with regard to the reactor equipment. When the reaction is complete, the aqueous phase has to be separated off and extracted, the organic phase must be dried and in most cases the solvent has to be distilled off before distillation of the end product. This is time consuming and expensive.

According to Z. Lebensm. Unters. Forsch. 1980, 34–35, one version of this process comprises dehydrating the intermediate, 4-hydroxytetrahydrothiopyran-3-carboxaldehyde, in the presence of a molecular sieve, a yield of 86% being obtained.

It is an object of the present invention to provide a process which is technically simple to carry out and does not have the above disadvantages.

We have found that this object is achieved by an advantageous process for the preparation of 5,6-dihydro-2H-thiopyran-3-carboxaldehydes of the formula

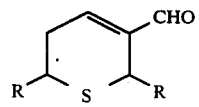

where R is hydrogen or methyl, wherein acrolein or crotonaldehyde is reacted with hydrogen sulfide in a mineral oil whose boiling point is higher than those of the starting materials and of the end product, and the 5,6-dihydro-2H-thiopyran-3-carboxaldehyde is obtained by distillation.

Using this process, it is possible to prepare 5,6-dihydro-2H-thiopyran-3-carboxaldehydes in short reaction times, under atmospheric pressure, in high purity (>95%) and in yields of about 90%, without its being necessary to carry out drying or to distill off solvents. Polymeric constituents or decomposition products remain in the solvent, which can be disposed of by combustion, without further working up. This process therefore avoids the use of chlorohydrocarbons as a reaction medium and saves time and costs in comparison with the conventional processes. A further advantage is that only a small amount of a non-corrosive organic acid is required in the dehydration stage.

In a preferred embodiment of the process according to the invention, in a first stage, acrolein or crotonaldehyde is reacted with hydrogen sulfide without the addition of a catalyst at from 20° to 60° C. in the mineral oil and, in a second stage, the adduct, without prior working up, is cyclized and dehydrated in the presence of a high boiling acidic substance at from 70° to 130° C., the water liberated is distilled off under atmospheric or reduced pressure, and the end product is obtained by distillation under reduced pressure.

Specifically, acrolein or crotonaldehyde is reacted with hydrogen sulfide in a high boiling hydrocarbon as solvent by feeding hydrogen sulfide and acrolein simultaneously into a reactor, which may consist of a stirred kettle or cylindrical reactors, eg. bubble columns or packed columns. While hydrogen sulfide is passed in as a gas, acrolein or crotonaldehyde may be metered in as a liquid or gas. The molar ratios of acrolein or crotonaldehyde to hydrogen sulfide can be varied from 3.0:1 to 1.5:1 but is preferably from 2.2:1 to 1.8:1. It is also possible initially to take acrolein or crotonaldehyde in the mineral oil and then to pass in the required amount of hydrogen sulfide.

Examples of suitable mineral oils whose boiling point is higher than that of the starting materials or of the end product are gas oil, fuel oil, molten paraffin wax and aromatic hydrocarbon oils. Advantageously, vacuum gas oil having a boiling point of not less than 350° C., in particular a boiling range of from 350° to 500° C., is used as the mineral oil.

The adduct of acrolein or crotonaldehyde with hydrogen sulfide is formed as an intermediate, without the addition of a catalyst, at from −20° to +200° C., preferably from +20° to +60° C., under atmospheric pressure.

Cyclization and dehydration of the adduct can be carried out without prior working up, in the presence of a high boiling acidic substance.

Preferably, an aliphatic or aromatic sulfonic acid, in particular a mixture of aliphatic sulfonic acids containing $C_{10}$–$C_{30}$-alkyl radicals, benzenesulfonic acid, toluenesulfonic acid or dodecylbenzenesulfonic acid, is used as a catalyst. The amounts added are from 0.0001 to 10, preferably from 0.01 to 5, in particular from 0.1 to 1, mol%. The reaction is advantageously carried out at from +70° to +130° C., in particular from +100° to +120° C., the water liberated being distilled off, preferably simultaneously, in a gentle stream of nitrogen under reduced pressure of about 15 mbar or under atmospheric pressure. 5,6-Dihydro-2H-thiopyran-3-carboxaldehyde or the corresponding 2,5-dimethyl compound is then obtained as a very pure (>95%) end product in a yield of about 90% by distillation from the mineral oil under, for example, from 0.1 to 1 mbar.

For economic reasons, the mineral oil is not worked up after the reaction. Hence, the part removed, or the entire amount of mineral oil containing the sparingly volatile byproducts, is advantageously burned in a power station.

The Examples which follow illustrate the process according to the invention. Parts are by weight.

EXAMPLE 1

100 parts/hour of acrolein and 30 parts/hour of hydrogen sulfide are passed, at from 40° to 50° C., into a stirred flask charged with 1,000 parts of vacuum gas oil. After 2 hours, the feed of materials is terminated and the mixture is stirred for a further 30 minutes, after which 10 parts of dodecylbenzenesulfonic acid are added and the mixture is heated at from 100° to 120° C. in a gentle stream of nitrogen (from 15 to 20 l/hour), water liberated being distilled off. The reaction is complete after about 1.5 hours, and the desired product is then distilled off from the vacuum gas oil under reduced pressure of from 0.1 to 1 mbar. 207 parts (90.5% yield) of 5,6-dihydro-2H-thiopyran-3-carboxaldehyde are obtained.

EXAMPLE 2

The procedure described in Example 1 is followed, except that 1,000 parts of vacuum residues are used instead of vacuum gas oil. 201 parts (87.9% yield) of 5,6-dihydro-2H-thiopyran-3-carboxaldehyde are obtained.

EXAMPLE 3

The procedure described in Example 1 is followed, except that 100 parts/hour of acrolein and 27 parts/hour of hydrogen sulfide are reacted. 185 parts (yield 91.1%, based on hydrogen sulfide employed) of 5,6-dihydro-2H-thiopyran-3-carboxaldehyde are obtained.

EXAMPLE 4

The procedure described in Example 1 is followed, except that 100 parts/hour of acrolein and 35 parts/hour of hydrogen sulfide are reacted. 196 parts (yield 85.7%, based on acrolein employed) of 5,6-dihydro-2H-thiopyran-3-carboxaldehyde are obtained.

EXAMPLE 5

200 parts of acrolein in 1,000 parts of vacuum gas oil are initially taken, and 60 parts of hydrogen sulfide are passed in at from 40° to 50° C. in the course of 2 hours. 10 parts of dodecylbenzenesulfonic acid are then added, and the procedure is continued as described in Example 1. 184 parts (80.5% yield) of 5,6-dihydro-2H-thiopyran-3-carboxaldehyde are obtained.

EXAMPLE 6

After the addition of 20 l/hour of nitrogen, 100 parts/hour of acrolein are vaporized in an evaporator heated at 70° C. and are fed in gaseous form, simultaneously with 30 parts of hydrogen sulfide, into 1,000 parts of vacuum gas oil heated at from 40° to 50° C. and contained in a stirred flask. The evaporator consists of an oil-heated coil condenser. The procedure is continued as described in Example 1.

197 parts (86.2% yield) of 5,6-dihydro-2H-thiopyran-3-carboxaldehyde are obtained.

EXAMPLE 7

After the addition of 20 l/hour of nitrogen, 100 parts/hour of acrolein are vaporized in an evaporator (oil-heated coil condenser) heated at 70° C. and are fed in gaseous form, simultaneously with 30 parts of hydrogen sulfide, into the reactor which is charged with 1,000 parts of vacuum gas oil heated at from 40° to 50° C. and circulated continuously. The reactor consists of an oil-heated double-walled tube having a length of 1,300 mm and an internal diameter of 60 mm. The feed of materials is terminated after 2 hours, and the mixture is heated at from 100° to 120° C. in a gentle stream of nitrogen (from 15 to 20 l/hour), water liberated being distilled off. The reactor content is then transferred to a distillation apparatus, and the desired product is distilled off from the vacuum gas oil under from 0.1 to 1 mbar. 204 parts (89.2% yield) of 5,6-dihydro-2H-thiopyran-3-carboxaldehyde are obtained.

EXAMPLE 8

200 parts/hour of crotonaldehyde and 49 parts/hour of hydrogen sulfide are passed, at from 40° to 50° C., into a stirred flask charged with 1,000 parts of vacuum gas oil. The feed of materials is terminated after 2 hours, and stirring is continued for 30 minutes. 20 parts of dodecylbenzenesulfonic acid are added and the mixture is heated at about 110° C. in a gentle stream of nitrogen (from 15 to 20 l/hour), water liberated being distilled off. The product is then distilled off from the vacuum gas oil under reduced pressure of from 0.1 to 1 mbar (bp.=73°–76° C./0.6; $n_D^{25}$=1.5265). 407 parts (91.3% yield) of 2,5-dimethyl-5,6-dihydro-2H-thiopyran-3-carboxaldehyde are obtained.

We claim:

1. A process for the preparation of a 5,6-dihydro-2H-thiopyran-3-carboxaldehyde of the formula

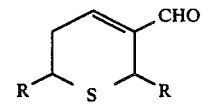

where R is hydrogen or methyl, wherein, in a first stage, acrolein or crotonaldehyde is reacted with hydrogen sulfide without the addition of a catalyst at from 20° to 60° C. in a mineral oil whose boiling point is higher than those of the starting materials and of the end product, the acrolein or crotonaldehyde and hydrogen sulfide being fed simultaneously into the reactor in a molar ratio of from 3:1 to 1.5:1 and, in a second stage, the adduct, without prior working up, is cyclized and dehydrated in the presence of a high boiling acidic substance at from 70° to 130° C., the water liberated is distilled off under atmospheric or reduced pressure, and the 5,6-dihydro-2H-thiopyran-3-carboxaldehyde is obtained by distillation under reduced pressure, some or all of the mineral oil used, instead of being recovered, being fed for combustion in a power station when the reaction is complete.

2. A process as claimed in claim 1, wherein the mineral oil used is vacuum gas oil having a boiling point of not less than 350° C.

3. A process as claimed in claim 1, wherein acrolein or crotonaldehyde and hydrogen sulfide are fed simultaneously into the reactor in a molar ratio of from 3:1 to 1.5:1.

4. A process as claimed in claim 1, wherein acrolein or crotonaldehyde and hydrogen sulfide are fed simultaneously into the reactor in a molar ratio of from 2.2:1 to 1.8:1.

5. A process as claimed in claim 1, wherein gaseous hydrogen sulfide and liquid or gaseous acrolein or crotonaldehyde are fed into the reactor.

6. A process as claimed in claim 1, wherein the high boiling acidic substance is a high boiling aliphatic or aromatic sulfonic acid.

7. A process as claimed in claim 1, wherein the high boiling aliphatic or aromatic sulfonic acid is tridecylsulfonic acid or dodecylbenzenzenesulfonic acid.

* * * * *